(12) United States Patent
Oscarson et al.

(10) Patent No.: US 8,992,963 B2
(45) Date of Patent: Mar. 31, 2015

(54) IMMOBILISED BIOLOGICAL ENTITIES (75) Inventors: Stefan Oscarson, Stockholm (SE);
Martina Lahmann, Stockholm (SE);
Karin Leontein, Upplands Väsby (SE);
Robert Vestberg, Upplands Väsby (SE)

(73) Assignee: Carmeda AB, Upplands Vasby (SE)

(*) Notice: Subject to any disclaimer, the term of this patent is extended or adjusted under 35 U.S.C. 154(b) by 675 days.

(21) Appl. No.: 12/559,660

(22) Filed: Sep. 15, 2009

(65) Prior Publication Data

US 2010/0074938 A1  Mar. 25, 2010

(30) Foreign Application Priority Data

Sep. 15, 2008 (GB) .................................. 0816783.5

(51) Int. Cl.
| | |
|---|---|
| A61K 9/00 | (2006.01) |
| A61K 31/727 | (2006.01) |
| A61P 7/02 | (2006.01) |
| A61K 31/715 | (2006.01) |
| A61L 27/34 | (2006.01) |
| A61L 27/54 | (2006.01) |
| A61L 33/00 | (2006.01) |

(52) U.S. Cl.
CPC ................ *A61L 27/34* (2013.01); *A61L 27/54* (2013.01); *A61L 33/0029* (2013.01); *A61L 2300/42* (2013.01); *A61L 2300/608* (2013.01)
USPC .............. 424/423; 424/400; 424/422; 514/56

(58) Field of Classification Search
USPC .............................. 424/400, 423, 424; 514/56
See application file for complete search history.

(56) References Cited

U.S. PATENT DOCUMENTS

| | | | |
|---|---|---|---|
| 2,818,376 A | 12/1957 | Foulke et al. | |
| 4,613,665 A | 9/1986 | Larm | |
| 5,049,043 A | 9/1991 | Nakajima | |
| 5,049,403 A * | 9/1991 | Larm et al. ...................... | 427/2.1 |
| 5,213,898 A | 5/1993 | Larm et al. | |
| 6,461,665 B1 * | 10/2002 | Scholander .................. | 427/2.24 |
| 6,653,457 B1 | 11/2003 | Larm et al. | |
| 7,375,234 B2 | 5/2008 | Sharpless et al. | |
| 2003/0175408 A1 * | 9/2003 | Timm et al. ..................... | 427/2.1 |
| 2004/0170752 A1 | 9/2004 | Luthra et al. | |
| 2004/0234575 A1 | 11/2004 | Horres et al. | |
| 2005/0032081 A1 * | 2/2005 | Ju et al. .............. | 435/6 |
| 2005/0059068 A1 | 3/2005 | Huang et al. | |
| 2005/0222427 A1 | 10/2005 | Sharpless et al. | |
| 2005/0266038 A1 * | 12/2005 | Glauser et al. ................. | 424/423 |
| 2007/0020620 A1 | 1/2007 | Finn et al. | |
| 2007/0154521 A1 | 7/2007 | Zhao | |
| 2007/0264308 A1 | 11/2007 | Cleek et al. | |
| 2008/0089919 A1 * | 4/2008 | Cleek et al. .................. | 424/423 |
| 2008/0311412 A1 | 12/2008 | Fokin et al. | |
| 2009/0018646 A1 | 1/2009 | Zhao | |

FOREIGN PATENT DOCUMENTS

| | | |
|---|---|---|
| DE | 19604173 | 8/1997 |
| EP | B-0086186 | 5/1986 |
| EP | B-0086187 | 9/1990 |
| EP | B-0495820 | 5/1995 |
| EP | 1152013 | 7/2001 |
| EP | 115203 A | 11/2001 |
| EP | 1806373 | 7/2007 |
| EP | 2014308 | 1/2009 |
| FR | 2920435 | 7/2008 |
| GB | 1508823 | 4/1978 |
| JP | 03188868 | 8/1991 |
| WO | 00/13719 | 3/2000 |
| WO | 0160415 | 8/2001 |
| WO | 2003024897 | 3/2003 |
| WO | 2004/055160 | 7/2004 |
| WO | 2006/012569 | 2/2006 |
| WO | 2007/003054 | 1/2007 |
| WO | 2007/011696 | 1/2007 |
| WO | 2007/035296 | 3/2007 |
| WO | 2008019450 | 2/2008 |
| WO | 2008/031525 | 3/2008 |
| WO | 2008090555 | 7/2008 |
| WO | 2009027454 | 3/2009 |

OTHER PUBLICATIONS

Miura, et al., "The Self-Assembled Monolayer of Saccharide via Click Chemistry: Formation and Protein Recognition", Thin Solid Films, 2008; 516: 2443-2449.

Jones, et al., "Phospine-Mediated One-pot Thiole-ENE "click" approach to Polymer-Protein Conjugates", Chem. Commun. 2009; 5272-5274.

Pasche, et al., "Binding of Antithrombin to Immobilized Heparin Under Varying Flow Conditions", Artificial Organs, 1991; 15(6): 481-491.

Nie, et al., "Production of Heparin-Containing Hydrogels for Modulating Cell Responses" Acta Biomaterialia, 2009; 5: 865-875.

Lih, et al., "An in Situ Gel-Forming Heparin-Conjugated PLGA-PEG-PLGA Copoymer" Journal of Bioactive and Compatible Polymers, 2008; 23:444-457.

Kristensen, et al., "Characterization of Heparin Surfaces using Photoelectron Spectroscopy and Quartz Crystal Microbalance", Biomaterials, 2003; 24: 4153-4159.

Jing, et al., "Preparation and Characterization of Heparin-Modified Gold Nanoparticles", Journal of Rehabilitative Tissue Engineering Research, 2009, 13(8): 1521-1524.

Iha, et al., Applications of Orthogonal "Click" Chemistries in the Synthesis of Functional Soft Materials, Chem. Rev. 2009; 109: 5620-5686.

(Continued)

*Primary Examiner* — Anoop Singh
*Assistant Examiner* — Anna Falkowitz
(74) *Attorney, Agent, or Firm* — Klauber & Jackson LLC (57) ABSTRACT

There is described inter alia a medical device having a surface which comprises a coating layer, said coating layer being a biocompatible composition comprising an entity capable of interacting with mammalian blood to prevent coagulation or thrombus formation, which entity is covalently attached to said surface through a link comprising a 1,2,3-triazole.

15 Claims, 5 Drawing Sheets

(56) References Cited

OTHER PUBLICATIONS

Baskin, J.M.—"Bioorthogonal Click Chemistry: Covalent Labeling in Living Systems," QSAR Comb. Sci. 26, 2007, No. 11-12, 1211-1219.

Wilkinson et al.—"Synthetic utility of glycosyl triazoles in carbohydrate chemistry," Tetrahedron (2006) 62, 8115-8125.

Sun, Xue-Long—"Carbohydrate and Protein Immobilization onto Solid Surfaces by Sequential Diels—Alder and Azide Alkyne Cycloadditions," Bioconjugate Chem., 2006, 17, 52-57.

Hotha, Sprinivas, "'Click chemistry' inspired synthesis of pseudo-oligosaccharides and amino acid glycoconjugates," J Org Chem., 2006 71(1), 364-367.

Dedola, S.—"Recent applications of the Cu(I)-catalysed Huisgen azide alkyne 1,3-dipolar cycloaddition reaction in carbohydrate chemistry," Org Biomol Chem, 2007, 5, 1006-1017.

Dodoni, A.—"Triazole: the keystone in glycosylated molecular architectures constructed by a click reaction," Chem Asian J., 2007, 2, 700-708.

Zhang, Yun—"Carbohydrate-Protein Interactions by "Clicked" Carbohydrate Self-Assembled Monolayers," Anal Chem. 2006, 78, 2001-2008.

Michel, O.—"Carbohydrate microarrays by microcontact 'click' chemistry," Langmuir, 2008, 24, 12116-12118.

Decher, et al—"Multilayer Thin Films," Pub. Wiley-VCH, Ed. Decher and Schlenoff (2003) ISBN: 3-527-30440-1.

Sanchez, Jr., "Inhibition of the plasma contact activation system of immobilized heparin: Relation to surface density of functional antithrombin binding sites," J Biomed Mat Res 1997, 37(1) 37-42.

Liu et al., "New Approaches for the Preparation of Hydrophobic Heparin Derivatives," Journal of Pharmaceutical Sciences, 1994; 83(70):1034-1039.

Poulin-Kerstien et al., "DNA-Templated Dimerization of Hairpin Polyamides," J. Am. Chem. Soc. 2003; 125:15811-15821.

* cited by examiner

IMMOBILISED BIOLOGICAL ENTITIES

RELATED APPLICATION

The present application claims the priority of GB Application Serial No. 0816783.5, filed Sep. 15, 2008. The disclosure of the aforementioned application is incorporated by reference herein in its entirety, and applicants claim the benefits of this application under 35 U.S.C. §119.

BACKGROUND OF THE INVENTION

This invention relates to immobilised biological entities, surfaces, e.g. of medical devices, coated with such entities, and processes and intermediates for their production.

When a medical device is placed in the body, or in contact with body fluids, a number of different reactions are set into motion, some of them resulting in the coagulation of the blood in contact with the device surface. In order to counteract this serious adverse effect, the well-known anti-coagulant compound heparin has for a long time been administered systemically to patients before the medical device is placed in their body, or when it is in contact with their body fluids, in order to provide an antithrombotic effect.

Thrombin is one of several coagulation factors, all of which work together to result in the formation of thrombi at a surface in contact with the blood. Antithrombin (also known as anti-thrombin III) ("AT") is the most prominent coagulation inhibitor. It neutralizes the action of thrombin and other coagulation factors and thus restricts or limits blood coagulation. Heparin dramatically enhances the rate at which antithrombin inhibits coagulation factors.

However, systemic treatment with high doses of heparin is often associated with serious side-effects of which bleeding is the predominant. Another rare, but serious complication of heparin therapy is the development of an allergic response called heparin induced thrombocytopenia that may lead to thrombosis (both venous and arterial). High dose systemic heparin treatment e.g. during surgery also requires frequent monitoring of the activated clotting time (used to monitor and guide heparin therapy) and the corresponding dose adjustments as necessary.

Therefore solutions have been sought where the need for a systemic heparinisation of the patient would be unnecessary or can be limited. It was thought that this could be achieved through a surface modification of the medical devices using the anti-coagulative properties of heparin. Thus a number of more or less successful technologies have been developed where a layer of heparin is attached to the surface of the medical device seeking thereby to render the surface non-thrombogenic. For devices where long term bioactivity is required, heparin should desirably be resistant to leaching and degradation.

Heparin is a polysaccharide carrying negatively charged sulfate and carboxylic acid groups on the saccharide units. Ionic binding of heparin to polycationic surfaces was thus attempted, but these surface modifications suffered from lack of stability resulting in lack of function, as the heparin leached from the surface.

Thereafter different surface modifications have been prepared wherein the heparin has been covalently bound to groups on the surface.

PRIOR ART

One of the most successful processes for rendering a medical device non-thrombogenic has been the covalent binding of a heparin fragment to a modified surface of the device. The general method and improvements thereof are described in European patents: EP-B-0086186, EP-B-0086187, EP-B-0495820 and U.S. Pat. No. 6,461,665.

These patents describe the preparation of surface modified substrates by first, a selective cleavage of the heparin polysaccharide chain, e.g. using nitrous acid degradation, leading to the formation of terminal aldehyde groups. Secondly, the introduction of one or more surface modifying layers carrying primary amino groups on the surface of the medical device, and thereafter reacting the aldehyde groups on the polysaccharide chain with the amino groups on the surface modifying layers followed by a reduction of the intermediate Schiffs bases to form stable secondary amine bonds.

However there is still a requirement for surface modifications which are more easily manipulated, are simpler and more efficient to produce and/or where the bioavailability of the heparin moiety is higher.

Baskin et at QSAR Comb. Sci. 26, 2007, No. 11-12, 1211-1219 describe the use of the reaction of azides with alkynes for the covalent labeling of biomolecules in cells and living organisms, but play down its use because of the toxic nature of the copper used to catalyze the reaction.

US patent applications 20070020620, 20050032081 and 20050222427 relate to the use of a similar reaction to attach biomolecules to various other molecules.

WO2007/003054 (Shoichet) discloses the immobilization of biomolecules on polymers. Specifically, biodegradable polymers are mentioned (page 1, line 13). Reaction of an alkyne with an azide to form a triazole is illustrated. However application to the preparation of compositions having anti-coagulant function is not envisaged. Moreover use of a triazole to achieve linkage of a biomolecule to the surface of any medical device is not envisaged either.

EP1806373 (Cordis) describes a neutral tri-branched polymer for coating medical devices. The polymer is typically dip or spray-coated onto the device which is not pre-treated in any way. The preferred heparin to be employed is low molecular weight (i.e. degraded) heparin. The disclosure appears speculative and although a process for attachment of heparin to the polymer scaffold is shown in Scheme 1, the suggested product (shown as structure III) seems unlikely to be produced since the NHS moiety of the molecule that is reacted with heparin should be displaced by a primary amino group not a hydroxyl group. Heparin contains very few primary amino groups, unless these are generated through chemical processing, and none is located at the end-point of the molecule.

US2009/0018646 (Zhao), published after the claimed priority date of this application, describes a biodegradable or bioabsorbable neutral polymer having heparin moieties linked thereto via a 1,2,3-triazole. The polymer is typically dip or spray-coated onto the device which may bear a first drug-bearing polymer layer but otherwise is not pre-treated in any way. The heparin employed is typically either low molecular weight heparin (see claim 3) or desulfated heparin (see claim 4) to reveal amino groups (not being at the end point of the molecule) which are used as the point of attachment to the polymer. This reaction is not practically suitable for use with native heparin which contains hardly any primary amino groups.

We have now found a simple method of covalently attaching entities capable of interacting with mammalian blood to prevent coagulation or thrombus formation, e.g. heparin, and especially full length heparin rather than the degraded heparin of the prior art, to a surface.

SUMMARY OF THE INVENTION

According to the invention we provide, inter alia, a medical device having a surface which comprises a coating layer, said coating layer being a biocompatible composition comprising an entity capable of interacting with mammalian blood to prevent coagulation or thrombus formation (herein "entity" or "entities" or "anti-coagulant entity" or "anti-coagulant entities"), which entity is covalently attached to said surface through a link comprising a 1,2,3-triazole.

BRIEF DESCRIPTION OF THE FIGURES

FIG. 1 shows photographs of examples of PVC tubing where the luminal side is coated with nitrous acid degraded heparin or native heparin under various conditions according to the invention as described in Example 1.5a.

FIG. 5 illustrates the azide functionalization of Polymin SN, as described in Example 2a.

DETAILED DESCRIPTION OF THE INVENTION

Such entities are well known to those skilled in the art and many of them are oligosaccharides or polysaccharides. Some of the entities are glycosaminoglycans including compounds containing glucosamine, galactosamine, and/or uronic acid. Preferred glycosaminoglycans are "heparin moieties" and especially full length heparin (i.e. native heparin).

The term "heparin moiety" refers to a heparin molecule, a fragment of the heparin molecule, or a derivative or analogue of heparin. Heparin derivatives can be any functional or structural variation of heparin. Representative variations include alkali metal or alkaline earth metal salts of heparin, such as sodium heparin (e.g., Hepsal or Pularin), potassium heparin (e.g., Clarin), lithium heparin, calcium heparin (e.g., Calciparine), magnesium heparin (e.g., Cutheparine), and low molecular weight heparin (prepared by e.g. oxidative depolymerization or deaminative cleavage, e.g. Ardeparin sodium or Dalteparin). Other examples include heparan sulfate, heparinoids, heparin based compounds and heparin having a hydrophobic counter-ion. Other desirable entities include synthetic heparin compositions referred to as "fondaparinux" compositions involving antithrombin III-mediated inhibition of factor Xa. Additional derivatives of heparin include heparins and heparin moieties modified by means of e.g. periodate oxidation (U.S. Pat. No. 6,653,457) and other modification reactions know in the art. Heparin moieties also include such moieties bound to a linker or spacer as described below. De-sulphated heparin is less preferred because of its reduced bioactivity relative to other forms of heparin.

We prefer the heparin moiety to be single point attached. We prefer the single point to be end point attached. We also prefer the end point attached heparin to be connected through its reducing end (sometimes referred to herein as position C1 of the reducing terminal). The advantage of end point attachment, especially reducing end point attachment, is that it is expected that the biological activity of the heparin moiety is maximized due to enhanced availability of the thrombin interaction sites as compared with attachment elsewhere in the heparin moiety.

Where there are a multiplicity of entities e.g. heparin moieties it is possible for some or all of them to be of a different type; however we prefer them all to be of the same type.

At its simplest the link consists of the triazole ring only. However more usually the triazole ring will be separated by a spacer from either the surface or the heparin moiety or both. The Mw (molecular weight) of the link is suitably from $10^2$ to $10^6$ Da. The length of the link is suitably from 10 to $10^3$ Å. We prefer the links and/or spacers to be straight chain(s). It is also possible (although less preferred) for several, i.e. more than one, e.g. from 2 to 100, preferably 30 to 100 entities (e.g. heparin moieties) to be attached to a single link thus producing a branched link in which there are several heparin moiety side chains. In some embodiments the linker includes one or more aromatic rings. In other embodiments the linker does not include any aromatic rings except the triazole ring. In some embodiments the linker is hydrophilic, for example, it may comprise a PEG chain. In one aspect, the link may be viewed as having three portions—"link A" between the surface and the triazole moiety, the triazole moiety, and "link B" between the triazole moiety and the entity. In one embodiment the molecular weight of link A is between $10^1$ and $10^3$ Da. In another embodiment the molecular weight of link B is between $10^1$ and $10^3$ Da. In one embodiment link A comprises one or more aromatic rings. In another embodiment link A does not comprise any aromatic rings. In one embodiment link B comprises one or more aromatic rings. In another embodiment link B does not comprise any aromatic rings. In one embodiment link A is hydrophilic. In another embodiment link B is hydrophilic. In one embodiment link A comprises a PEG chain. In another embodiment link B comprises a PEG chain. In one embodiment links A and B are both hydrophilic, for example they each comprise a PEG chain. As used herein, a PEG chain refers to a polymeric chain obtainable by polymerisation of ethylene oxide, typically of weight between $10^2$ and $10^6$ Da. In another aspect, the link may comprise two or more triazole rings. For example, as described in the Examples, use of a bifunctional linker moiety (such as a bis-azide) can be connected at each end, respectively, to an alkyne functionalized entity and an alkyne functionalized surface resulting in the link containing two triazole rings. Alternatively, use of a bis-alkyne linker can be connected at each end, respectively, to an azide functionalized entity and an azide functionalized surface also resulting in the link containing two triazole rings. Thus in another embodiment, the link may be viewed as having five portions—"link A" between the surface and a first triazole moiety, the first triazole moiety, "link B" between the first triazole moiety and a second triazole moiety, the second triazole moiety, and "link C" between the triazole moiety and the entity. In one embodiment the molecular weight of link A is between $10^1$ and $10^3$ Da. In one embodiment the molecular weight of link B is between $10^2$ and $10^6$ Da. In one embodiment the molecular weight of link C is between $10^1$ and $10^3$ Da. In one embodiment link A and/or link B and/or link C is hydrophilic for example comprising a PEG chain. For example link B (at least) may comprise a PEG chain.

Thus suitably the link between the anti-coagulant entity such as a heparin moiety and the surface is an unbranched link and specifically does not include a branch of a hydrophobic or hydrophilic polymeric moiety. If a branch is to be included suitably it is only a branch containing another anti-coagulant entity such as a heparin moiety.

The link can be biodegradable or non-biodegradable. We prefer the link to be non-biodegradable in order that a coated medical device is non-thrombogenic for a long period of time.

Where there is a multiplicity of links it is possible for some or all of them to be of a different type; however we prefer all the links to be of the same type.

The surface may comprise a coating layer on a solid object, e.g. a shaped object such as a device, and more particularly a medical device. The solid object may have one or more portions containing void spaces, or pores. The pores may be within the object and/or comprising at least one surface of the object. An example of a porous solid object is expanded polytetrafluoroethylene (ePTFE).

The solid object may carry one or more, e.g. 2 or more, or 3 or 4 or 5 e.g. up to 20 coating layers such that desirably a portion of the surface (desired to be nonthrombogenic) or the whole of the surface of the object is covered (Multilayer Thin Films ISBN: 978-3-527-30440-0). The optimum number of layers will depend on the type of material from which the solid object is made, and the contemplated use of the surface. The surface may, if desired, be made up layer by layer. The number and nature of the layers needed to provide a full coverage of the surface can be easily determined by those skilled in the art. The coating layer(s) may be formed by adsorbing on the surface of the solid object a high average molecular weight cationic polymer, e.g. a polyamine (e.g. that known as Polymin available from BASF, see also EP 0086187 Larsson and Gölander) and if needed cross-linking the polyamine with, e.g. an aldehyde crosslinker such as crotonaldehyde and/or glutaraldehyde, followed by the application of a solution of an anionic polymer, e.g. an anionic polysaccharide, e.g. dextran sulfate, to obtain at least one adsorbed layer of the polysaccharide. Hence the surface may comprise a layer of high average molecular weight polyamine and a layer of anionic polysaccharide. More generally, the surface may comprise one or more coating bilayers of cationic polymer (e.g. polyamine) and anionic polymer (e.g. anionic polysaccharide), the innermost layer being a layer of cationic polymer and the outermost layer being a layer of cationic polymer covalently attached to the entity. This coating procedure is performed essentially as described in EP-B-0495820. Thus it is only the outer coating layer which is attached to the entity. Typically the outer coating later which is attached to the entity is not cross-linked.

The procedure of EP-B-0495820 may however be modified so that the outer layer is the anionic polysaccharide which is then reacted, as described below, with a polyamine to which the entity or an azide or alkyne is attached.

Prior to applying the first coating layer the surface of the solid object, e.g. the medical device, may be cleaned to improve adhesion and surface coverage. Suitable cleaning agents include solvents as ethanol or isopropanol (IPA), solutions with high pH like solutions comprising a mixture of an alcohol and an aqueous solution of a hydroxide compound (e.g. sodium hydroxide), sodium hydroxide solution as such, solutions containing tetramethyl ammonium hydroxide (TMAH), acidic solutions like Piranha (a mixture of sulfuric acid and hydrogen peroxide), and other oxidizing agents including combinations of sulfuric acid and potassium permanganate or different types of peroxysulfuric acid or peroxydisulfuric acid solutions (also as ammonium, sodium, and potassium salts).

Thus an aspect of the invention is a medical device having a surface wherein the surface comprises one or more coating bilayers of cationic polymer and anionic polymer, the innermost layer being a layer of cationic polymer and the outermost layer being a layer of cationic polymer covalently attached to the entity.

Another aspect of the invention is a non-thrombogenic medical device having a surface comprising a functionalized cationic polymer outer layer whereby an anti-coagulant entity is attached to the cationic polymer outer layer by means of a link comprising a 1,2,3-triazole.

Another aspect of the invention is a non-thrombogenic medical device which is obtainable by a process comprising:
(a) treating a medical device to present a cationic polymer surface layer which has been functionalized to bear azido groups;
(b) reacting said cationic polymer surface layer which has been functionalized to bear azido groups with an anti-coagulant entity which is functionalized to bear an alkyne group;
thereby to attach the anti-coagulant entity to the device through a link comprising a 1,2,3-triazole.

Another aspect of the invention is a non-thrombogenic medical device which is obtainable by a process comprising:
(a) treating a medical device to present a cationic polymer surface layer which has been functionalized to bear alkyne groups;
(b) reacting said cationic polymer surface layer which has been functionalized to bear alkyne groups with an anti-coagulant entity which is functionalized to bear an azido group;
thereby to attach the anti-coagulant entity to the device through a link comprising a 1,2,3-triazole.

Another aspect of the invention is a non-thrombogenic medical device which is obtainable by a process comprising:
(a) treating a medical device to present a cationic polymer surface layer;
(b) associating with said cationic polymer surface layer a functionalized cationic polymer bearing a plurality of negatively charged anti-coagulant entities such as heparin moieties which are attached thereto via a link comprising a 1,2,3-triazole said cationic polymer bearing a plurality of negatively charged anti-coagulant entities having a net negative charge.

As described above, the cationic polymer surface may be prepared by treating the device with a high average molecule weight cationic polymer such as a polyamine and if necessary cross-linking it with e.g. an aldehyde cross-linker. Further layers may optionally be built up by successive steps of (i) application of a solution of anionic polymer (e.g. anionic polysaccharide) to obtain an absorbed layer of the anionic polymer and (ii) then further treating that with functionalized cationic polymer, such as a polyamine, to provide an absorbed outer layer of functionalized cationic polymer, the outermost layer being functionalized to bear azido groups or alkyne groups.

Typically the first step of treating the device with a high average molecule weight cationic polymer is preceded by the step of cleaning the surface of the device with suitable cleaning agents (e.g. those mentioned above) or other methods of surface pretreatment known in the art to improve adherence and coverage of the first layer e.g. polyamine layer.

Another aspect of the invention is a non-thrombogenic medical device which is obtainable by a process comprising:
(a) treating a medical device to present an anionic polymer surface layer;
(b) associating with said anionic polymer surface layer a functionalized cationic polymer bearing a plurality of negatively charged anti-coagulant entities such as a heparin moieties which are attached thereto via a link comprising a 1,2,3-triazole said functionalized cationic polymer bearing a plurality of negatively charged anticoagulant entities having a net positive charge.

As described above, the device which presents an anionic polymer surface layer is typically prepared by treating the device with a high average molecule weight cationic polymer, such as a polyamine, optionally with cross-linking, followed by treating the polyamine surface with a solution of anionic polymer (e.g. anionic polysaccharide) to obtain an absorbed outer layer of the anionic polymer. Further layers may be built up by successive steps of (i) application of a cationic polymer (optionally with cross-linking) to provide an absorbed layer of cationic polymer and (ii) then treating that with a solution of anionic polymer (e.g. anionic polysaccharide) to obtain an absorbed outer layer of the anionic polymer.

Suitably the anionic polymer is a polysaccharide such as dextran sulfate or a derivative thereof.

As used herein a "polyamine" is a molecule having multiple (e.g. 10, 100, 1000 or more) free pendant amino groups preferably containing at least some primary amino groups. Polyamines are typically polymeric molecules having multiple amino groups of high average molecular weight, for example having an average molecular weight of $10^3$-$10^6$Da. An exemplary polyamine is a polyethyleneimine such as that known as Polymin available from BASF.

The cationic polymer may be functionalized using techniques known in the art. As illustrated in the Examples below, primary amino groups on the polyamine may be used as points of attachment for the alkyne or azido group. However a skilled person would know how to adapt the chemistry to use secondary amino groups on the polyamine as points of attachment for the alkyne or azido group. Hence polyamines may be functionalized to bear alkyne or azido groups by conventional means e.g. by reacting pendant primary amino groups on the polyamine with an activated carboxylic acid (e.g. an N-hydroxy succinimide derivative of a carboxylic acid) which acid bears an alkyne or azido group. Another way is to react secondary amines with carboxylic acids with carbodiimide chemistry or to react with carboxylic acid chlorides where the carboxylic acid portion bears an alkyne or azido group.

The entity, e.g. heparin, carrying an alkyne or azido group may be made by conventional methods known per se. For example an entity, e.g. heparin, carrying an alkyne group may be made by the reaction of an alkoxyamine (i.e. molecule of formula R—O—NH$_2$) carrying an alkyne or azido group with an aldehyde or hemi-acetal group on the entity using conventional techniques known per se or by methods analogous to those given in the Examples. The connection is formed via an oxy-imine function (R—O—N=R' in which R' is heparin). Nitrous acid degraded heparin bears an aldehyde group and native heparin contains a hemi-acetal function at their reducing end which may be linked in this way. The entity, e.g. heparin, carrying an azido group may also be made by reacting the alkyne functional heparin moiety with an excess of a difunctional azide (e.g. a PEG diazide). A person skilled in the art will be able to design other ways of introducing an azide or an alkyne functional group to the reducing end of a carbohydrate chain.

When a coating layer is used, the surface of all and any solid objects is transformed to present the same functionalized outer surface for the subsequent attachment of an entity capable of interacting with mammalian blood to prevent coagulation or thrombus formation. Hence a specific advantage of the processes described herein is that generally a very uniform non-thrombogenic surface is created (see FIGS. 1 and 3).

The solid object may be, for example a synthetic or naturally occurring organic or inorganic polymer or material such as polyethylene, polypropylene, polyacrylate, polycarbonate, polyamide, polyurethane (PU), polyvinylchloride (PVC), polyetherketone (PEEK), cellulose, silicone or rubber (polyisoprene), plastics materials, metals, glass, ceramics and other known medical materials or a combination of such materials. Other suitable substrate materials include fluoropolymers, e.g expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), and combinations of the above with and without crosslinking between the polymer chains.

Suitable metals include nickel titanium alloy (Nitinol), stainless steel, titanium, cobalt chromium, gold and platinum. Nitinol and stainless steel are preferred. Titanium is also preferred.

The solid object is suitably a medical device. The medical device can be implantable or non-implantable. Examples of implantable or non-implantable medical devices include catheters, stents, stent-grafts, artificial blood vessels, blood indwelling monitoring devices, artificial heart valves, pacemaker electrodes, guidewires, cardiopulmonary bypass circuits, cannulae, balloons, tissue patch devices, blood pumps, and extracorporeal devices, e.g. extracorporeal blood treatment devices, and transfusion devices.

We prefer the coated surface to which the entity (e.g. heparin or other heparin moiety) is attached to be such that it retains non-thrombogenic properties after sterilization, e.g. ethylene oxide (EO) sterilization.

Sterilization may be carried out by means well known to those skilled in the art. The preferred method of sterilization is using ethylene oxide gas. Alternatively, other methods such as radiation, e.g. e-beam or gamma radiation, may be used where such radiation will not degrade the object or the coating or both.

A preferred embodiment of the present invention relates to a coated medical device for implantation e.g. permanent implantation, or other placement, at an anatomical site. Other preferred embodiments include temporary use devices such as catheters and extracorporeal circuits. Examples are sterile (e.g. sterilized) medical devices for placement inside an anatomical structure delimiting a void space, or lumen, to reinforce the anatomical structure or maintain the void space. Suitably the attached entity, e.g. heparin or other heparin moiety, does not elute to any substantial extent and remains with the device. For example, the retained AT binding activity remains adequate (e.g. greater than 2 or 4 or 5 or 10 pmol/cm$^2$) and when tested in the Blood loop evaluation test (see Example 1.5a) with 15 hour NaCl (0.15 M) rinse prior to testing with fresh blood from a healthy donor the reduction in platelet count of the blood after the test is substantially lower for the blood exposed to the coated surface than that of an uncoated control (e.g. the reduction in platelet count after the test for the blood exposed to the coated surface is less than 20%, preferably less than 15% and more preferably less than 10%).

Suitably the biocompatible composition of the invention is not biodegradable or bioabsorbable. For biodegradable or bioabsorbable compositions the non-thrombogenic properties may generally be expected to be limited in time.

The non-thrombogenic character of devices according to the present invention may be tested by a number of methods. For example non-thrombogenic character may be associated with having a high antithrombin binding activity, especially as compared with devices having untreated surfaces.

For example, we prefer the surface, e.g. of the medical device, to have an antithrombin (AT) binding activity of at least 2 e.g. at least 5 picomoles AT per square centimeter (pmol/cm$^2$) of surface. In other embodiments, the AT binding activity is at least 6 pmol/cm$^2$, at least 7 pmol/cm$^2$, at least 8 pmol/cm$^2$, at least 9 pmol/cm$^2$, or at least 10 pmol/cm$^2$ of surface. In some embodiments, the AT binding activity is at least 100 pmol/cm$^2$ of surface. AT binding activity can be measured by methods known in the art, e.g. those described in Pasche., et al., in "Binding of antithrombin to immobilized heparin under varying flow conditions" Artif.-Organs 15:481-491 (1991) and US 2007/0264308. By way of comparison it may be concluded from Sanchez et al (1997) J. Biomed. Mater. Res. 37(1) 37-42, see FIG. 1, that AT binding values of around 2.7-4.8 pmol/cm$^2$ (depending on the experimental set up) or more do not appear to give rise to significant thrombogenic enzymatic activity upon contact with plasma.

Alternatively or additionally we prefer the surface to be non-thrombogenic due to high capacity to suppress coagulation and other defense systems in the Blood loop evaluation test described in Example 1.5a. According to that test, the surface to be investigated is applied to a PVC tubing which is rinsed for 15 hours with 0.15M NaCl prior to testing with fresh blood. Non-thrombogenicity is indicated by a reduction in platelet count of the blood measured after the test which is substantially lower for the blood exposed to the surface prepared according the method described herein than that of an uncoated control (e.g. the reduction in platelet count after the test for the blood exposed to the coated surface is less than 20%, preferably less than 15% and more preferably less than 10%).

Other similar blood evaluation methods different from the Blood loop model can be performed by those skilled in the art in order to assess thrombogenicity/non-thrombogenicity.

The amount of the entity bound to a particular surface area can be controlled and adjusted, e.g. by adjusting the amount of the reagents used in the synthesis of the composition.

The distribution of the entity on the surface can be determined by conventional staining techniques which are known per se, e.g. the distribution of heparin can be determined using toluidine blue.

According to the invention we also provide a process for the production of an entity capable of interacting with mammalian blood to prevent coagulation or thrombus formation, which entity is covalently bound to a surface through a link comprising a 1,2,3-triazole, which process comprises the reaction of a corresponding entity carrying an alkyne group with a corresponding surface carrying an azido group, or the reaction of a corresponding entity carrying an azido group with a corresponding surface carrying an alkyne group.

This process may be carried out using procedures known per se.

The surface carrying an azido group or an alkyne group may be made by conventional methods known per se, e.g. by reacting a surface, e.g. a surface as described in EP-B-0086186 or EP-B-0086187 carrying negatively charged sulfate groups with an appropriate polyamine carrying either an azide or an alkyne group respectively.

According to the invention we also provide a polyamine carrying an entity through a link comprising a 1,2,3-triazole.

In one embodiment in which the reaction is used the surface carries the azido group. In another embodiment in which the reaction is used the entity carries the azido group.

The reaction may be carried out in the presence of a metal catalyst, for example a copper, e.g. a Cu(I) catalyst using reaction conditions conventionally used in the Huisgen cycloaddition (the 1,3-dipolar cycloaddition of an azide and a terminal alkyne to form a 1,2,3-triazole). The Cu(I) catalyst may, if desired, be produced in situ, e.g. by reduction of a corresponding Cu(II) compound for example using sodium ascorbate. The reaction may also, if desired, be carried out under flow conditions.

As noted in the Prior Art section in connection with the Baskin disclosure, others have commented on the possible toxic nature of the Cu(I) catalyst used to catalyze this reaction. However as shown in Example 1.8, our coating appears to be non-toxic. Without being limited by theory, it is possible that either any residual Cu(I) catalyst is washed away from the surface or else the polyamine surface complexes it thus rendering it unable to exert any toxic effect.

The reaction may, for example be carried out at a temperature of from about 5 to 80° C., preferably at about room temperature. The pH used in the reaction may be from about 2-12, preferably about 4-9 and most preferably at about 7. Suitable solvents include those in which the entity attached to the azide or alkyne is soluble, e.g dimethylsulfoxide, dimethylformamide, tetrahydrofuran and preferably water or mixtures of water with one of the above. The proportion of the entity to the surface may be adjusted to provide the desired density of the entity on the surface. We prefer to use a proportion of the reagents such that no free azide or alkyne groups remain on the resulting surface.

By this new method the entity, e.g. heparin, can advantageously be bound to the surface by surface groups that are not involved in the build up of the surface covering. By contrast, the prior art described in EP-B-0086186, EP-B-0086187 and EP-B-0495820 uses the same type of groups (primary amines) in the layer by layer surface coating process as those used to bind the heparin to the coating.

This new process tends to be less sensitive to pH than are the prior art processes which is also advantageous.

According to the invention we also provide an entity, e.g. heparin or other heparin moiety, which entity carries an alkyne or an azido group. We also provide a heparin moiety capable of interacting with mammalian blood to prevent coagulation or thrombus formation which entity carries an alkyne or an azido group, which alkyne or azido group is attached to a linker, wherein the linker is end-point attached to the heparin moiety. The heparin moiety is suitably a full length heparin moiety (i.e. native heparin).

According to the invention we also provide a functionalized polyamine surface, e.g. a surface prepared essentially as described in EP-B-0086186, EP-B-0086187 and, EP-B-0495820, but additionally carrying one or more azide or one or more alkyne groups on the outermost layer of polyamine.

According to the invention we also provide a medical device having a polyamine surface carrying an azide or an alkyne group e.g. an azide or alkyne group which is connected to an amino group of the polyamine surface via a link.

According to a further feature of the invention we also provide a process for the production of an entity capable of interacting with mammalian blood to prevent coagulation or thrombus formation, which entity is covalently bound to a surface through a link comprising a 1,2,3-triazole, wherein the surface comprises one or more layers of polysaccharide (i.e. anionic polysaccharide) and polyamine, which process comprises the reaction of a corresponding surface having an outer layer of polysaccharide (i.e. anionic polysaccharide e.g. carrying negatively charged sulfate groups) with a polyamine carrying a corresponding entity through a link comprising a 1,2,3-triazole, or the reaction of a corresponding surface having an outer layer of polysaccharide (i.e. anionic polysaccharide e.g. carrying negatively charged sulfate groups) with a polyamine carrying an azide or alkyne group and reacting the resulting product with an entity carrying an alkyne or azido group respectively.

This process for putting down the layers of polysaccharide and polyamine may be carried out using procedures known per se, for example procedures analogous to those described in EP-B-0495820.

According to the invention we also provide a functionalized polyamine, e.g. Polymin which carries one or more azide or one or more alkyne groups e.g. via a linker.

According to the invention we also provide a functionalized polyamine carrying an entity attached thereto through a link comprising a 1,2,3-triazole. This polyamine may be made by procedures known per se, e.g. analogous to those described elsewhere in this specification.

The products of the invention may have one or more of the following advantageous properties:

The degree of substitution of the entity on the surface can be controlled;

Both end-point (one point) attachment and multi-point attachment of the entity, e.g. heparin, can be achieved, although end point (especially reducing end point) attachment is preferred;

The linker length between the entity and the surface can be controlled;

Full length heparin can be used thus avoiding the cleavage of heparin and the waste of parts of the cleaved product involved in the prior art nitrous acid degradation of heparin;

When cleaving heparin, the antithrombin binding sequence can be destroyed in some of the fragments, therefore using full-length heparin or heparin linked via a spacer can also improve the bioavailability of the bound heparin;

A uniform distribution of the entity over the surface can be obtained;

The bioavailability of the entity can be controlled, e.g. by the use of different links (length, type);

A non-thrombogenic surface which does not leach heparin and therefore has long lifetime can be obtained.

Other aspects of the invention include a biocompatible composition comprising an entity capable of interacting with mammalian blood to prevent coagulation or thrombus formation which entity is covalently attached to a surface through a link comprising a 1,2,3-triazole.

The skilled person will appreciate that the biocompatible composition may be applied to any solid object, of which a medical device is just one example. Therefore according to another aspect of the invention there is provided a solid object having a surface comprising (e.g. coated with) such a biocompatible composition.

The Invention is Illustrated, but in No Way Limited, by the Following Examples

Example 1.1

Preparation of a Non-Thrombogenic Surface on Gold

A surface comprising layers of aminated polymer and sulfated polysaccharide having a functionalized aminated polymer outer layer is connected to functionalized heparin thereby forming a triazole ring.

A gold surface (on a quartz crystal microbalance (QCM) crystal) was pretreated using the method described by Larm et al in EP-B-0086186 and EP-495820 (layer-by-layer; polyelectrolyte charge interactions) ending with a layer of sulfated polysaccharide.

The gold surfaces was first cleaned with ethanol. The priming was built-up by alternated adsorption of a positively charged polyamine (Polymin) and negatively charged sulfated polysaccharide (dextran sulfate). The polyamine is crosslinked with a difunctional aldehyde (crotonaldehyde). Every pair of polyamine and sulfated polysaccharide is called one bilayer. The gold surface was primed with 3 bilayers ending with the sulfated polysaccharide.

Polymin SN (Lupasol SN; Lupasol is an alternative trade name for Polymin) was diluted with water to prepare a stock solution (5 g Polymin SN was added to 20 mL purified water). (Polymin is a polyethyleneimine cationic tenside available from BASF).

The complete process was carried out at a flow of 500 µL/min. in a Q-Sense E4 (http://www.q-sense.se/) system with a peristaltic pump (Ismatec IPC-N 4).

100 µL of a 5% solution of azide functionalized polyamine (preparation see Example 2a) was added to 100 ml, of a 0.04 M/0.04 M borate/phosphate buffer at pH 8.0. The adsorption of the azide functional polyamine to the sulfate surface was carried out for 10 minutes at room temperature. A two minute water rinse was performed after the adsorption to rinse off excess polymer.

50 mg of nitrite degraded heparin, with alkyne functionalization at C1 of the reducing terminal (prepared as in Example 3a), was dissolved in 200 mL of de-ionized water and 25 mg $CuSO_4 \times 5H_2O$, 50 mg sodium ascorbate and 2.9 g NaCl were added. The pH was measured to be 4.4.

The reaction between the solution of the alkyne functionalized heparin and the azide functionalized surface was carried out at room temperature for 1 h. Purification was performed by rinsing off non-covalently linked heparin for 10 minutes using a 0.04 M/0.04 M borate/phosphate buffer at pH 8.0. A final rinse with de-ionized water for two minutes was performed to wash away buffer salt residues.

Analytical Results:

Antithrombin binding activity of bound heparin: 21 pmol/$cm^2$

The antithrombin binding activity of bound heparin was measured essentially as described in Pasche., et al., in "Binding of antithrombin to immobilized heparin under varying flow conditions" Artif.-Organs 15:481-491 (1991).

Example 1.2

Preparation of a Non-Thrombogenic Surface on Gold

A surface comprising layers of aminated polymer and sulfated polysaccharide having a functionalized aminated polymer outer layer is connected to functionalized heparin thereby forming a triazole ring.

The process of Example 1.1 was repeated with slight variation of the parameters as follows: 200 µL, (2 mL/L) of a 5% solution of azide functionalized polyamine (prepared as in Example 2a) was employed;

The adsorption of the azide functional polyamine to the sulfate surface was carried out for 20 minutes at room temperature;

50 mg (250 mg/L) $CuSO_4 \times 5H_2O$ and 100 mg (500 mg/L) sodium ascorbate were employed;

The pH was measured to be 4.8.

Finally, the antithrombin binding activity of bound heparin of the coated gold surface was measured as 30 pmol/cm².

Example 1.3

Comparison

Another identical gold surface was coated in the exact same way as described in Example 1.2 above except that no CuSO₄ as catalyst was added in the heparin coupling step. The antithrombin binding activity of bound heparin was negligible showing that if no covalent coupling occurs the heparin is rinsed off in the last buffer rinsing step.

Example 1.4

Preparation of a Non-Thrombogenic Surface on Gold

A gold surface was coated as in Example 1.2 using native heparin, with alkyne functionalization at C1 of the reducing terminal (prepared as in Example 3b) at pH 4.8 and also at pH 7 (pH adjusted with 1 M HCl and 1 M NaOH respectively).

The antithrombin binding activity of bound heparin of the coated gold surface was measured as 25 pmol/cm² for the surface prepared at pH 4.8 and 44 pmol/cm² when the preparation was performed at pH 7.

Example 1.5a

Preparation of a Non-Thrombogenic Surface on PVC

The luminal surface of a PVC tubing (I.D. 3 mm) was cleaned with isopropanol and an oxidizing agent. It was then primed as in Example 1.1 with 3 bilayers ending with sulfated polysaccharide. The priming was then reacted as in Example 1.2 first with an azide functionalized polyamine (prepared as in Example 2a) followed by reaction with nitrous acid degraded heparin, with alkyne functionalization at C1 of the reducing terminal (prepared as in Example 3a) at pH 4.8 and, separately, with native heparin, with alkyne functionalization at C1 of the reducing terminal (prepared as in Example 3b) at pH 4.8 and, separately, at pH 7. Purification was performed using the same buffer and water rinse as in Example 1.1. In both experiments, the flow used during the entire process was set to 100 mL/min. The antithrombin binding activity of bound heparin for the samples was tested and found to be acceptable (i.e above 2 pmol/cm²).

Figure 1:
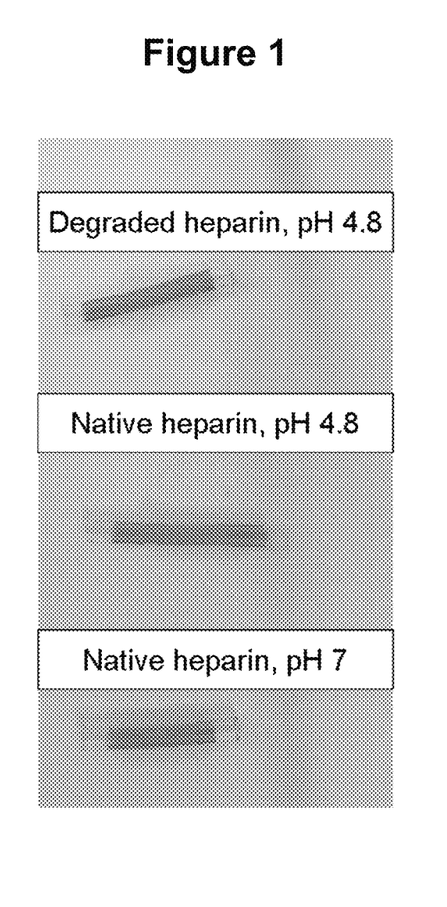

The samples were stained with toluidine blue ("TB") (200 mg/L in water) by immersing in the solution for 2 minutes followed by extensive water rinse. The TB attaches to the heparin via ionic interaction. As shown in FIG. 1, the stain is uniform showing that the heparin is evenly distributed over the surface.

The coated samples were analyzed again after storage at room temperature (more than 8 months) in an aluminum foil bag with a desiccant inside to show stability of the coating. The antithrombin binding activity of bound heparin for the samples after aging was tested and found to be acceptable (i.e above 2 pmol/cm²).

Blood Loop Evaluation Test

Blood loop evaluation was performed on these stored samples to show the preserved heparin bioactivity of the non-thrombogenic surface. First the luminal side of the coated tubings were washed with 0.15 M NaCl for 15 hours at a flow of 1 mL/min to ensure that all loosely bound heparin was rinsed off and a stable surface remains. Then the washed tubings were incubated in a Chandler loop model performed essentially according to Anderson et al. (Andersson, J.; Sanchez, J.; Ekdahl, K. N.; Elgue, G.; Nilsson, B.; Larsson, R. J Biomed Mater Res A 2003, 67(2), 458-466) at 20 rpm. The platelets, from fresh blood and from the blood collected from the loops, were counted in a cell counter to measure the loss of platelets which indicates thrombosis. As references were included a non-thrombogenic control (i.e Carmeda BioActive Surface® applied to PVC, which is prepared essentially as described in EP-B-0495820), an uncoated PVC tube, and a thrombogenic control (i.e. a three bilayer coating with an outer layer of sulfated polysaccharide not binding antithrombin).

As seen in the table below there is virtually no platelet loss (platelet loss indicates thrombosis) seen for the coatings prepared using the stored degraded and native heparin coatings prepared in this example (Example 1.5a). The uncoated PVC tubing and the surface with an outer layer of sulfated polysaccharides (not binding antithrombin) show significant thrombosis in this experiment.

| | Evaluated surfaces | Platelet count × 10⁹/L | Loss in platelet count % |
|---|---|---|---|
| Initial value, blood before Chandler loop | | 206 | |
| Evaluated surfaces according to the invention | Degraded heparin | 203 | 1 |
| | Native heparin | 190 | 8 |
| Reference surfaces | Non-thrombogenic control | 195 | 5 |
| | Uncoated PVC tube | 116 | 44 |
| | Thrombogenic control | 3 | 99 |

These results demonstrate the non-thrombogenic properties of the stable surface prepared according to the invention.

Example 1.5b

Comparison

Figure 2:
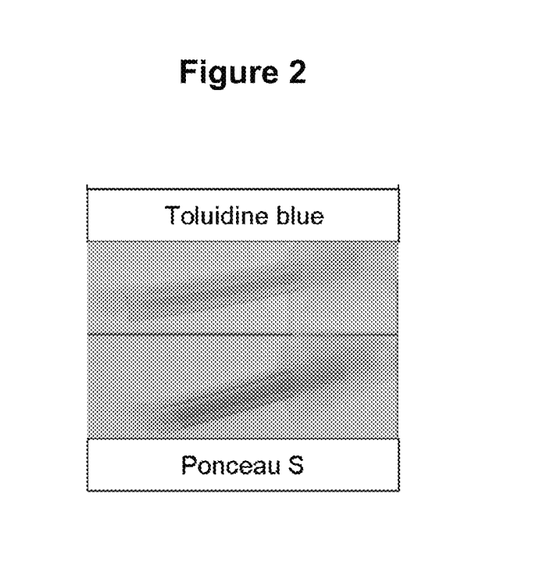
FIG. 2 shows photographs of examples of PVC tubing where the luminal side is processed as described in Example 1.5b and illustrating that these tubes are not properly coated with nitrous acid degraded heparin.

A variation on the process described in Example 1.5a was performed but now using a polyamine that was not functionalized with azides and a nitrous acid degraded heparin without an alkyne. The sample was stained with TB and also with Ponceau S (PS) using the procedure described above. The PS water solution contained 200 mg/L of PS and 5.75 mL/L of acetic acid. As shown in FIG. 2 (upper panel) no TB stain was seen after this alternative procedure. However, in FIG. 2 (lower panel) a red stain from the PS is seen which indicates the occurrence of an outer aminated layer. This shows that no heparin was attached after the alternative procedure and that all non-covalently linked heparin is washed off during the buffer rinse.

Example 1.6

Preparation of a Non-Thrombogenic Surface on Various Different Substrates

Different substrates (FEP, PTFE, silicone polymer, polyurethane (PU), stainless steel, and titanium) were cleaned with isopropanol and an oxidizing agent. They were then primed as in Example 1.1 with 4 bilayers ending with sulfated polysaccharide. The priming was then reacted as in Example 1.2 first with an azide functionalized polyamine (prepared as in Example 2a) followed by reaction with nitrous acid degraded heparin, with alkyne functionalization at C1 of the reducing terminal (prepared as in Example 3a) at pH 7 (adjusted with 1 M HCl and 1 M NaOH). Purification was performed using the same buffer and water rinse as in Example 1.1. The coating was performed by immersing the materials into the coating solutions.

Figure 3:
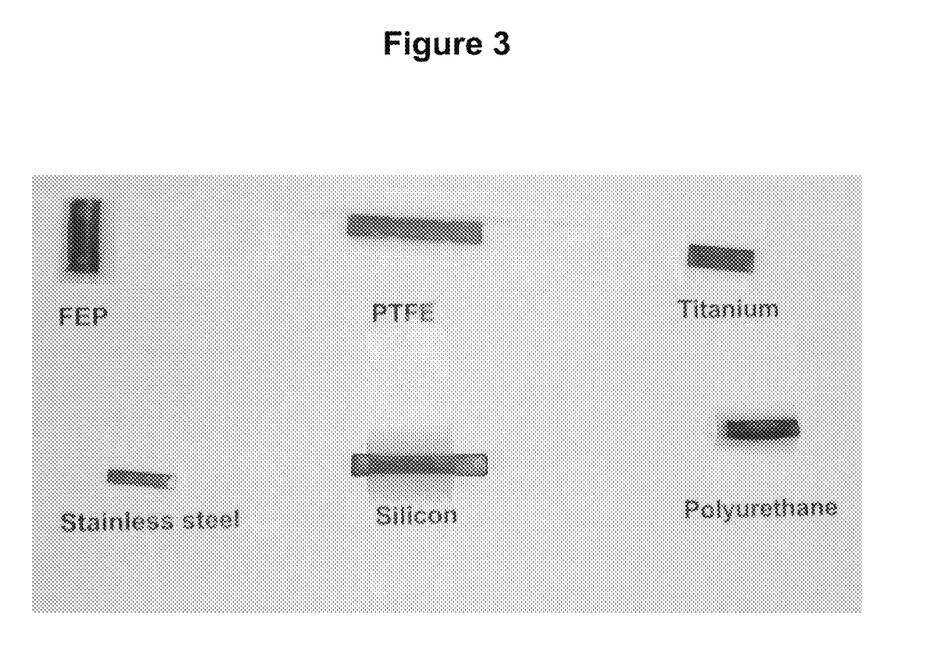
FIG. 3 shows photographs of examples of various different substrates coated with nitrous acid degraded heparin according to the invention as described in Example 1.6.
Figure 4:
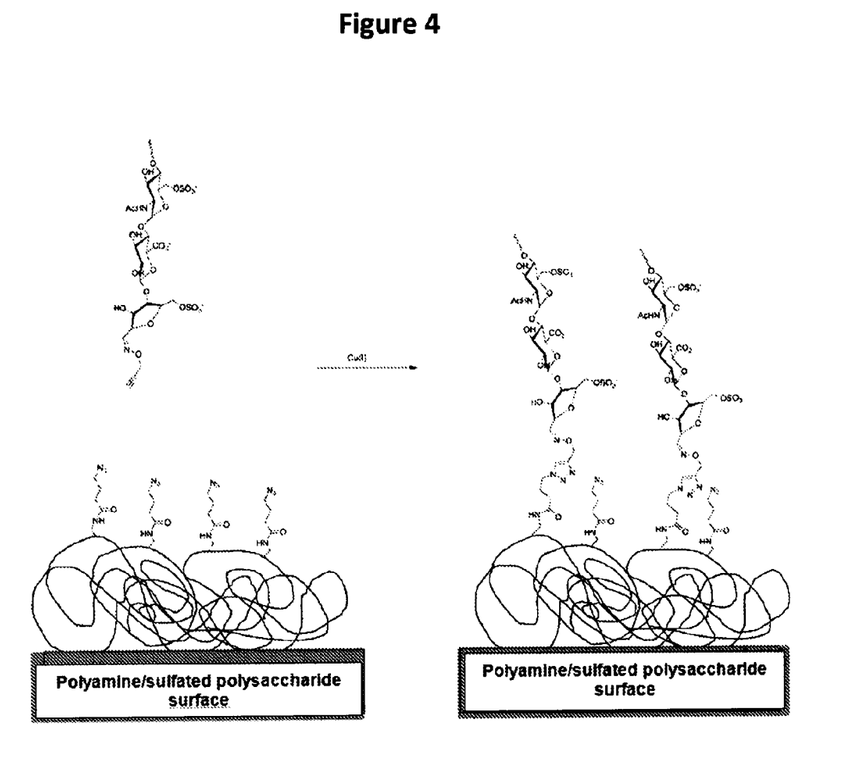
FIG. 4 illustrates the reaction between alkyne functionalized heparin and an azide functionalized surface, as described in Example 1.1.
Figure 5:
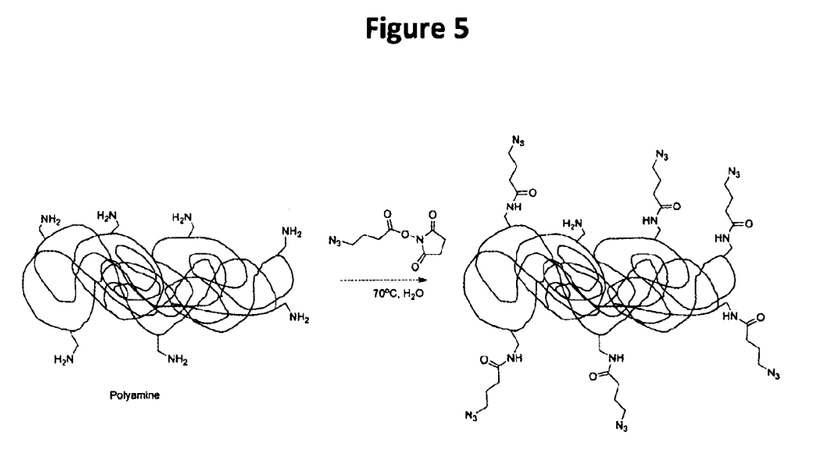
Figure 6:
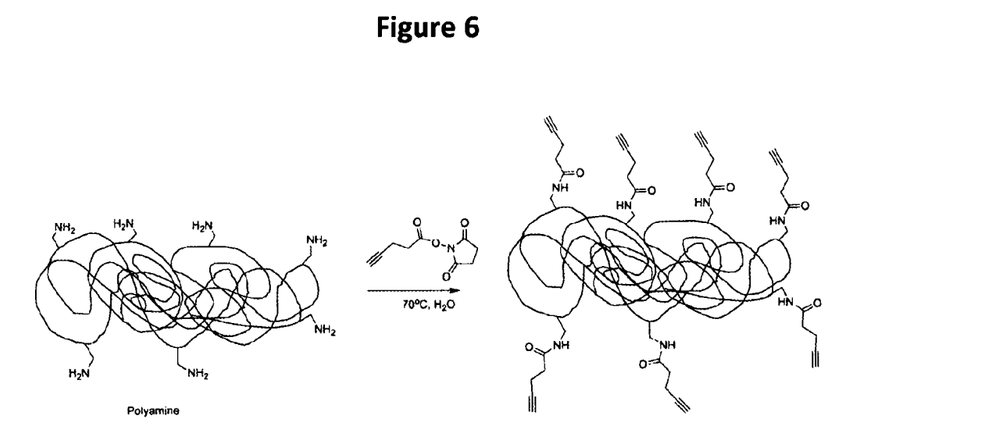
FIG. 6 illustrates the alkyne functionalization of Polymin SN, as described in Example 2b.

As can be seen from FIG. 3, staining with TB (as described in Example 1.5a) shows a uniform distribution of heparin on all the substrates (the small unstained spots are due to the fixturing of the materials).

The antithrombin binding activity of bound heparin for the different coated substrates are shown in the table below measured after sterilization by ethylene oxide (EO). The EO-sterilization was performed using a standard sterilization technique used for medical devices.

| Substrate | AT-uptake after EO-sterilization (pmol/cm$^2$) |
|---|---|
| FEP | 19 |
| PTFE | 7.3 |
| Titanium | 12 |
| Steel | 13 |
| Silicone | 7.6 |
| PU | 14 |

The data show that in spite of exposure to rigorous sterilization conditions the retained activity is still acceptable.

Example 1.7

Preparation of a Non-Thrombogenic Surface on a Medical Device

The luminal side of a Gore-Tex Vascular graft (thin wall, 5 mm diameter, catalog number: VT05070L) was cleaned with isopropanol. It was then primed as in Example 1.1 with 2 bilayers ending with sulfated polysaccharide. The priming was then reacted as in Example 1.2 first with an azide functionalized polyamine (prepared as in Example 2a) followed by reaction with nitrous acid degraded heparin, with alkyne functionalization at C1 of the reducing terminal (prepared as in Example 3a) at pH 7 (adjusted with 1 M HCl and 1 M NaOH). Purification was performed using the same buffer and water rinse as in Example 1.1. The flow used during the entire process was set to 30 mL/min. The heparin antithrombin uptake activity after EO-sterilization (conditions as in example 1.6) was measured as 8.7 pmol/cm$^2$.

The data show that in spite of exposure to rigorous sterilization conditions the retained activity is still acceptable.

Example 1.7b

Preparation of a Non-Thrombogenic Surface on a Medical Device

The method of Example 1.7a may be repeated using native heparin, modified with alkyne functionalization of the reducing terminal (prepared as in Example 3b or 3c) to give a graft coated with a non-thrombogenic surface comprising modified native heparin.

Example 1.8

Preparation of a Biocompatible Surface on a HDPE (High Density Poly Ethylene

An HDPE sheet (30 cm$^2$, USP reference standard) was cleaned by immersion into a solution of concentrated KMnO$_4$ (2 g/L) in concentrated H$_2$SO$_4$ for 2 minutes according to the method of EP 0086186 (Larm et al). The sheet was then primed as in Example 1.1 with 3 bilayers ending with sulfated polysaccharide. The priming was then reacted as in Example 1.2 first with an azide functionalized polyamine (prepared as in Example 2a) followed by reaction with nitrous acid degraded heparin, with alkyne functionalization at C1 of the reducing terminal (prepared as in Example 3a) at pH 7 (adjusted with 1 M HCl and 1 M NaOH). Purification was performed using the same buffer and water rinse as in Example 1.1. The coating was performed by immersing the materials into the coating solutions. The coating was found to be non-toxic in a cytotoxicity testing using the Minimal Essential Medium (MEM) elution test as described in ISO10993.

These results demonstrate the biocompatibility of the evaluated surface.

Example 1.9

Preparation of a Biocompatible Surface on PVC (Reversed Functionality and PEG Spacer)

The luminal surface of a PVC tubing (internal diameter 3 mm) was cleaned with isopropanol and an oxidizing agent. It was then primed with four bilayers of a positively charged polyamine (Polymin) and a negatively charged sulfated polysaccharide (dextran sulfate) ending with the sulfated polysaccharide.

Then next coating step used a solution of 2 mL of a 5% solution of alkyne functionalized polyamine (prepared as in Example 2b) in 1000 mL of a 0.04 M/0.04 M borate/phosphate buffer at pH 8.0. The adsorption of the azide functional polyamine to the sulfate surface was carried out for 15 minutes at room temperature. A two minute water rinse was performed after the adsorption to rinse off excess polymer.

Then a solution of 250 mg of heparin, with azide functionalization and a polyethylene glycol (PEG) spacer at C1 of the reducing terminal, 250 mg CuSO$_4$x5H$_2$O, 50 mg sodium ascorbate, and 2.9 g NaCl in 1000 mL of deionized water was used. The pH was adjusted to 7 (adjusted with 1 M HCl and 1 M NaOH).

Example 1.9a used nitrous acid degraded heparin with an azide functional group and a short PEG spacer prepared according to Example 4a.

Example 1.9b used nitrous acid degraded heparin with an azide functional group and a long PEG spacer prepared according to Example 4b.

Example 1.9c used native heparin with an azide functional group and a short PEG spacer prepared according to Example 4c.

Example 1.9d used native heparin with an azide functional group and a long PEG spacer prepared according to Example 4d.

The reaction between the solution with the azide functionalized heparin and the alkyne functionalized surface was carried out at room temperature for 1 h. Purification was performed by rinsing off non-covalently linked heparin for 10 minutes using a 0.04 M/0.04 M borate/phosphate buffer at pH 8.0. A final rinse with de-ionized water for two minutes was performed to wash away buffer salt residues.

Example 2a

Azide Functionalization of Polymin SN

Polymin SN (Lupasol SN; Lupasol is an alternative trade name for Polymin) was diluted with water to prepare a stock solution (5 g Polymin SN was added to 20 mL purified water). (Polymin is a polyethyleneimine cationic tenside available from BASF).

A solution of N-hydroxysuccinimide-azidobutyrate (Ref: Khoukhi; Vaultier; Carrie,—Synthesis and reactivity of methyl[gamma]-azido butyrates and ethyl[sigma]-azido valerates and of the corresponding acid chlorides as useful reagents for the aminoalkylation. *Tetrahedron* 1987, 43, (8), 1811-1822. and Malkoch, M.; Schleicher, K.; Drockenmuller, E.; Hawker, C. J.; Russell, T. P.; Wu, P.; Fokin, V. V., Structurally Diverse Dendritic Libraries: A Highly Efficient Functionalization Approach Using Click Chemistry. *Macromolecules* 2005, 38, (9), 3663-3678. (see also R. Kumar, A. El-Sagheer, J. Tumpane, P. Lincoln, L. M. Wilhelmsson, T. Brown, Journal of the American Chemical Society, 2007, 129(21) 6859-6864) (1.7 g, 7.5 mmol) in 10 mL of purified water was mixed with 24 mL of the Polymin SN (resulting in ~5 mmol of primary amines in the aqueous solution) and left to react overnight at 70° C. The reaction mixture was then diluted with water and isopropanol (min 99%, PhEur quality, Merck) until the polymer precipitated. The isopropanol was decanted off and the residual isopropanol of the resulting slurry was evaporated off. The functionalized polymer was analyzed by NMR and FTIR. The FTIR showed a typical signal from —N$_3$ at 2100 cm$^{-1}$.

Example 2b

Alkyne Functionalization of Polymin SN

Alkyne functional polyamine was prepared essentially as in Example 2a but using N-hydroxysuccinimide-(4-pentynoate) (Ref: Salmain, M.; Vessieres, A.; Butler, I. S.; Jaouen, G. *Bioconjugate Chemistry* 1991, 2(1), 13-15) instead of N-hydroxysuccinimide-azidobutyrate.

Example 3a

Preparation of Alkyne Functionalized Nitrous Acid Degraded Heparin

Reagents:
(i) Nitrous acid degraded heparin with aldehyde groups (prepared essentially as in Example 2 of U.S. Pat. No. 4,613,665) 3.25 g dry weight (0.65 mmol)
(ii) O-(prop-2-ynyl)-hydroxylamine hydrochloride (Ref: Xu, R.; Sim, M. K.; Go, M. L., Synthesis and pharmacological characterization of O-alkynyloximes of tropinone and N-methylpiperidinone as muscarinic agonists. *J Med Chem* 1998, 41, (17), 3220-3231) 0.70 g dry weight (6.5 mmol)
(iii) Acetic acid (100% Merck) 3 mL
(iv) Purified water 50 mL

The compounds were dissolved in the mixed solvents and the pH adjusted to 4.5 with 4M NaOH. The reaction was continued for 3 days at room temperature. The resulting product was dialyzed against purified water with a SpectraPor dialysis membrane mwco 1 kD (flat width 45 mm).

The functionalized product was analyzed by FTIR which showed a typical signal from the alkyne at 3100 cm$^{-1}$.

The activity of the functionalized heparin was 96 IU/mg which indicates that the activity of the functionalized heparin is substantially unaffected by functionalization.

Example 3b

Preparation of Alkyne Functionalized Native Heparin

The native heparin (SPL, Scientific Protein Laboratories, lot no. 1037) was functionalized according to the procedures described in Example 3a.

The activity of the functionalized heparin was 211 IU/mg which indicates that the activity of the functionalized heparin is substantially unaffected by functionalization.

Example 3c

Preparation of Alkyne Functionalized Native Heparin with Aromatic Spacer

The native heparin (SPL, Scientific Protein Laboratories, lot no. 1037) (20 mg) was dissolved in 250 µl acetic acid (100% Merck) and 250 µl purified water and 6 µl N-(4-(2-(aminoxy)ethyl)phenyl)pent-4-ynamide from stock solution (see Example 5 below) was added. The reaction was carried out at room temperature for 16 hrs. The reaction products were concentrated and co-evaporated with toluene (3×2 mL) to give a yellowish solid (~20 mg).

Example 4

Preparation of Azide Functionalized Nitrous Acid Degraded Heparin and Native Heparin with PEG Chain Link

Preparation of Intermediates

N-hydroxysuccinimidyl 4-azidobutyrate

The 4-azidobutyric acid derivative was prepared according to published procedures (N. Khoukhi, M. Vaultier, R. Carrie, Tetrahedron, 1987, 43(8) 1811-1822) followed by N-hydroxysuccinimide activation (R. Kumar, A. El-Sagheer, J. Tumpane, P. Lincoln, L. M. Wilhelmsson, T. Brown, Journal of the American Chemical Society, 2007, 129(21) 6859-6864).

ω-Azido Bifunctionalized Long PEG-Spacer (x~40, See Above)

To a solution of diamino functionalized PEG (O,O'-Bis(2-aminopropyl)polypropylene glycol-block-polyethylene glycol-block-polypropylene glycol 1900) (7.2 g; ~3.8 mmol; x~40) in 15 mL dichloromethane (DCM) was added N-hydroxysuccinimidyl 4-azidobutyrate (2.0 g, ~8.85 mmol). The reaction mixture was stirred at room temperature overnight, then diluted with DCM, and subsequently washed with 1 M HCl, NaHCO₃ (sat.) and brine. Drying (MgSO₄), concentration and drying under vacuum produced approx. 8 g of a slightly yellow solid. Identification of the reaction product with TLC and MALDI showed expected results.

ω-Azido Bifunctionalized Short PEG-Spacer (x~11, See Above)

To a solution of diamino functionalized PEG (O,O'-Bis(2-aminopropyl)polypropylene glycol-block-polyethylene glycol-block-polypropylene glycol 500) (2.4 g; ~3.9 mmol; x~11) in 10 mL dichloromethane (DCM) was added N-hydroxysuccinimidyl 4-azidobutyrate (2.0 g, ~8.85 mmol). The reaction mixture was stirred at room temperature over night then diluted with DCM, and subsequently washed with 1 M HCl, NaHCO₃ (sat.) and brine. Drying (MgSO₄), concentration and drying under vacuum produced approx. 3.1 g of an oily product. Identification of the reaction product with TLC and MALDI showed expected results.

Preparation of Azido Functionalized Heparin with Spacer (Reversed Functionality)

Example 4a

The ω-azido bifunctionalised short PEG (800 mg, ~1.0 mmol) was dissolved in deionized water (35 mL), then alkyne functionalized nitrous acid degraded heparin (500 mg, ~0.1 mmol), see Example 3a, was added together with CuSO₄x5H₂O (100 mg) and sodium ascorbate (160 mg). The reaction mixture was then stirred for 2 days followed by dialysis for 3 days against purified water with a SpectraPor dialysis membrane mwco 1 kD (flat width 45 mm length 50 cm). The dialyzed product in approximately 200 mL of water was filtered over a 20 μm filter plate and freeze dried to yield 620 mg. The activity of the azide functionalized nitrous acid degraded heparin with short PEG spacer was 96 IU/mg (calculated based on the carbohydrate part) which indicates that the activity of the functionalized heparin is substantially unaffected by functionalization.

Example 4b

The ω-azido bifunctionalised long PEG (2.0 g, ~1.0 mmol) was dissolved in deionized water (20 mL), then alkyne functionalized nitrous acid degraded heparin (500 mg, ~0.1 mmol), see Example 3a. was added together with CuSO₄x5H₂O (100 mg) and sodium ascorbate (160 mg). The reaction mixture was then stirred for 2 days followed by dialysis for 3 days against purified water with a SpectraPor dialysis membrane mwco 1 kD (flat width 45 mm length 50 cm). The dialyzed product in approximately 600 mL of water was freeze dried to yield 1.8 g. The activity of the azide functionalized nitrous acid degraded heparin with long PEG spacer was 93 IU/mg (calculated based on the carbohydrate part) which indicates that the activity of the functionalized heparin is substantially unaffected by functionalization.

Example 4c

The ω-azido bifunctionalised short PEG (800 mg, ~1.0 mmol) was dissolved in deionized water (35 mL), then alkyne functionalized native heparin (1.0 g, ~0.1 mmol), see Example 3b, was added together with CuSO₄x5H₂O (100 mg) and sodium ascorbate (160 mg). The reaction mixture was then stirred for 2 days followed by dialysis for 3 days against purified water with a SpectraPor dialysis membrane mwco 1 kD (flat width 45 mm length 50 cm). The dialyzed product in approximately 200 mL of water was filtered over a 20 μm filter plate and freeze dried to yield 900 mg. The activity of the azide functionalized native heparin with short PEG spacer was not measured.

Example 4d

The ω-azido bifunctionalised long PEG (1.0 g, ~0.5 mmol) was dissolved in deionized water (15 mL), then alkyne functionalized native heparin (450 mg, ~0.05 mmol), see Example 3b, was added together with CuSO₄x5H₂O (50 mg) and sodium ascorbate (80 mg). The reaction mixture was then stirred for 2 days followed by dialysis for 3 days against purified water with a SpectraPor dialysis membrane mwco 1 kD (flat width 45 mm length 40 cm). The dialyzed product in approximately 100 mL of water was freeze dried to yield 840 mg. The activity of the azide functionalized native heparin with long PEG spacer was 181 IU/mg (calculated based on the carbohydrate part) which indicates that the activity of the functionalized heparin is substantially unaffected by functionalization.

Example 5

Bifunctional Linker

5a) N-(4-(2-(hydroxy)ethyl)phenyl)pent-4-ynamide

N-hydroxysuccinimide-(4-pentynoate) (Ref: Malkoch, M.; Schleicher, K.; Drockenmuller, E.; Hawker, C. J.; Russell, T. P.; Wu, P.; Fokin, V. V., Structurally Diverse Dendritic Libraries: A Highly Efficient Functionalization Approach Using Click Chemistry. *Macromolecules* 2005, 38, (9), 3663-3678.) (200 mg, 1.0 mmol) and p-aminophenylethanol (125 mg, 0.9 mmol) were dissolved in 2 mL of dichloromethane together with triethyl amine (140 μL, 1.0 mmol), and 5 drops of dimethyl formamide. The reaction mixture was stirred at room temperature for 2 hours. The crude reaction product was concentrated, dissolved in 10 mL of ethyl acetate and washed with 5 mL of water followed by, 5 mL of 0.5 M HCl (aq.), 5 mL of 10 NaHCO$_3$ (aq.) and finally 5 mL of water. The organic phase was dried with MgSO$_4$, filtered, and the solvent was evaporated. The product was further purified by column chromatography on silica gel eluting with a gradient of toluene (T) and ethyl acetate (E) from 4:1 to 1:2 (T:E). The product N-(4-(2-(hydroxy)ethyl)phenyl)pent-4-ynamide was characterized by NMR and MALDI-TOF.

5b) N-(4-(2-(methanesulfonate)ethyl)phenyl)pent-4-ynamide

N-(4-(2-(hydroxy)ethyl)phenyl)pent-4-ynamide (210 mg, 1.0 mmol) was dissolved in 4 mL of pyridine. Methanesulfonyl chloride (MsCl) (100 μL, 1.3 mmol) was added at 0° C. The stirred reaction was brought back to room temperature and reacted at room temperature for 5 min. The solvent was evaporated and the residue re-dissolved in 10 mL of ethyl acetate and washed with 5 mL of water followed by 5 mL of 0.1 M HCl (aq.), and finally 5 mL of water. The organic phase was dried with MgSO$_4$, filtered, and the solvent was evaporated to yield the product N-(4-(2-(methanesulfonate)ethyl)phenyl)pent-4-ynamide.

5c) N-(4-(2-(N-oxyphthalimide)ethyl)phenyl)pent-4-ynamide

The N-(4-(2-(methanesulfonate)ethyl)phenyl)pent-4-ynamide was dissolved in 6 mL of acetonitrile and added to a solution of N-hydroxyphthalimide (200 mg, 0.9 mmol) and triethyl amine (250 μl, 1.8 mmol) in 2 mL acetonitrile. The reaction mixture was stirred at 50° C. for 2 days. The reaction mixture was then diluted with 40 mL of ethyl acetate and washed with 20 mL of 0.5 M HCl (aq.), 5×30 mL of 10 NaHCO$_3$ (aq.) to remove the red color, and finally 5 mL of water. The organic phase was dried with MgSO$_4$, filtered, and the solvent was evaporated. The crude product was re-crystallized from 10 mL of toluene to obtain N-(4-(2-(N-oxyphthalimide)ethyl)phenyl)pent-4-ynamide which was characterized by NMR and MALDI-TOF.

5d) N-(4-(2-(aminoxy)ethyl)phenyl)pent-4-ynamide

N-(4-(2-(N-oxyphthalimide)ethyl)phenyl)pent-4-ynamide (20 mg, 5.5 μmol) and ethylenediamine (200 μL, 3.0 mmol) was dissolved in 2 mL of ethanol. The reaction was stirred at 75° C. for 2 hours. The solvent was evaporated and the crude product purified by column chromatography on silica gel eluting with a gradient of toluene (T) and ethyl acetate (E) from 2:1 to 1:3 (T:E). The product N-(4-(2-(aminoxy)ethyl)phenyl)pent-4-ynamide was characterized by NMR and MALDI-TOF.

Preparation of Stock Solution:

N-(4-(2-(aminoxy)ethyl)phenyl)pent-4-ynamide (2.5 mg) was placed in a metric flask and acetonitrile (1000 μL) was added to dissolve the linker.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention embraces all combinations of preferred and more preferred groups and suitable and more suitable groups and embodiments of groups recited above.

The invention claimed is:

1. A medical device having a surface which comprises a coating layer, said coating layer being a biocompatible composition comprising a heparin moiety which is covalently end point attached through position C1 of its reducing terminal to said surface through a link comprising a 1,2,3-triazole wherein the device has an antithrombin III binding activity of at least 2 picomoles antithrombin III per square centimeter (pmol/cm$^2$) of surface.

2. A device according to claim 1, wherein the heparin moiety is a full length heparin.

3. A device according to claim 1, wherein the surface comprises two or more coating layers, only the outer coating layer being attached to the heparin moiety.

4. A device according to claim 1 wherein the surface comprises one or more coating bilayers of cationic polymer and anionic polymer, the innermost layer being a layer of cationic polymer and the outermost layer being a layer of cationic polymer covalently attached to the heparin moiety.

5. A device according to claim 1, comprising a multiplicity of links of the same type.

6. A device according to claim 1, wherein more than one heparin moiety is attached to each link.

7. A device according to claim 1, wherein the coating comprises a polyamine as cationic polymer.

8. A device according to claim 7, wherein the coating comprises a layer of a high average molecular weight polyamine and a layer of an anionic polysaccharide as anionic polymer.

9. A device according to claim 7, wherein the polyamine is cross-linked.

10. A device according to claim 1, which device comprises a metal or a synthetic or naturally occurring organic or inorganic polymer.

11. A device according to claim 1, which device is a sterile medical device for implantation, or other placement, at an anatomical site.

12. A device according to claim 1, wherein the medical device has an antithrombin III binding activity of at least 5 picomoles e.g. at least 10 picomoles antithrombin III per square centimeter (pmol/cm$^2$) of surface.

13. A non-thrombogenic medical device having a surface comprising a functionalized cationic polymer outer layer whereby heparin moiety is end point attached at position C1 of its reducing terminal to the cationic polymer outer layer through a link comprising a 1,2,3-triazole wherein the device has an antithrombin III binding activity of at least 2 picomoles antithrombin III per square centimeter (pmol/cm$^2$) of surface.

14. A non thrombogenic medical device according to claim 13 wherein the cationic polymer is a polyamine.

15. A non thrombogenic medical device according to claim 13 wherein the heparin moiety is a full length heparin moiety.

* * * * *